(12) United States Patent
Miranda et al.

(10) Patent No.: US 10,067,080 B1
(45) Date of Patent: Sep. 4, 2018

(54) POLYMER NANOFIBER BASED REVERSIBLE NANO-SWITCH/SENSOR SCHOTTKY DIODE (NANOSSSD) DEVICE

(71) Applicant: The United States of America as represented by the Administrator of NASA, Washington, DC (US)

(72) Inventors: Felix A. Miranda, Olmsted Falls, OH (US); Onoufrios Theofylaktos, Avon Lake, OH (US); Nicholas Pinto, Caguas, PR (US); Carl H. Mueller, Strongsville, OH (US); Javier Santos-Perez, North Ridgeville, OH (US); Michael A. Meador, Strongsville, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 15/655,498

(22) Filed: Jul. 20, 2017

Related U.S. Application Data

(63) Continuation of application No. 14/672,673, filed on Mar. 30, 2015, now Pat. No. 9,753,001, which is a continuation-in-part of application No. 13/242,300, filed on Sep. 23, 2011, now Pat. No. 9,016,108.

(51) Int. Cl.
*G01N 7/00* (2006.01)
*G01N 27/12* (2006.01)
*H01L 51/42* (2006.01)
*H01L 51/05* (2006.01)

(52) U.S. Cl.
CPC ....... *G01N 27/129* (2013.01); *H01L 51/0575* (2013.01); *H01L 51/0579* (2013.01); *H01L 51/42* (2013.01)

(58) Field of Classification Search
None
See application file for complete search history.

(56) References Cited

U.S. PATENT DOCUMENTS

| | | | |
|---|---|---|---|
| 7,719,318 B1 | 5/2010 | Nordquist et al. | |
| 7,785,557 B2 | 8/2010 | Gruner et al. | |
| 7,944,728 B2 | 5/2011 | Nian et al. | |
| 2008/0170982 A1* | 7/2008 | Zhang | B82Y 10/00 423/447.3 |
| 2009/0174435 A1 | 7/2009 | Stan et al. | |
| 2009/0235721 A1 | 9/2009 | Robinson et al. | |
| 2009/0294759 A1 | 12/2009 | Woo et al. | |
| 2010/0021708 A1 | 1/2010 | Kong et al. | |
| 2010/0025660 A1 | 2/2010 | Jain et al. | |
| 2010/0055464 A1 | 3/2010 | Sung | |

(Continued)

*Primary Examiner* — Andre Allen
(74) *Attorney, Agent, or Firm* — Robert H. Earp, III; William M. Johnson

(57) ABSTRACT

A nanostructure device is provided and performs dual functions as a nano-switching/sensing device. The nanostructure device includes a doped semiconducting substrate, an insulating layer disposed on the doped semiconducting substrate, an electrode formed on the insulating layer, and at least one polymer nanofiber deposited on the electrode. The at least one polymer nanofiber provides an electrical connection between the electrode and the substrate and is the electroactive element in the device.

20 Claims, 10 Drawing Sheets

(56) References Cited

U.S. PATENT DOCUMENTS

| | | |
|---|---|---|
| 2010/0140723 A1 | 6/2010 | Kurtz et al. |
| 2010/0213435 A1 | 8/2010 | Fujii et al. |
| 2010/0218801 A1 | 9/2010 | Sung et al. |
| 2010/0255984 A1 | 10/2010 | Sutter et al. |
| 2010/0327847 A1 | 12/2010 | Leiber et al. |
| 2011/0048625 A1 | 3/2011 | Caldwell et al. |
| 2011/0059599 A1 | 3/2011 | Ward et al. |
| 2011/0066290 A1 | 3/2011 | Haddon et al. |
| 2011/0088320 A1 | 3/2011 | Marinero et al. |
| 2011/0089404 A1 | 4/2011 | Marcus et al. |
| 2011/0102088 A1 | 5/2011 | Bouchiat et al. |
| 2017/0327377 A1* | 11/2017 | Zhang .................. C01B 32/15 |

\* cited by examiner

POLYMER NANOFIBER BASED REVERSIBLE NANO-SWITCH/SENSOR SCHOTTKY DIODE (NANOSSSD) DEVICE

CROSS REFERENCE TO RELATED APPLICATIONS

This application is a Continuation Application claiming the benefit of priority from U.S. patent application Ser. No. 14/672,673, filed on Mar. 30, 2015, pending, which claims priority to U.S. patent application Ser. No. 13/242,300, entitled "Graphene Based Reversible Nano-Switch/Sensor Schottky Diode (nanoSSSD) Device", filed on Sep. 23, 2011, which Issued on Apr. 28, 2015 as U.S. Pat. No. 9,016,108 B1, each of which is hereby incorporated by reference in its entirety.

ORIGIN OF THE INVENTION

The invention described herein was made by an employee of the United States Government and may be manufactured and used only by or for the Government for Government purposes without the payment of any royalties thereon or therefore.

BACKGROUND

Developing technologies in support of monitoring the health of astronauts and the operation of critical instrumentation are ongoing in order to develop a better understanding of the changes in the human body and equipment anticipated in future space exploration. Accordingly, the emergence of promising technologies such as nanotechnology has sparked efforts to develop operational electronic and sensing devices at the nanoscale level with performance and sensing resolutions not yet achieved. These efforts have resulted in great specificity attained by tailoring the surface of sensors (i.e., surface modification) by optical, chemical and physical means (i.e., via the creation of preferred end-groups using approaches such as self-assembled monolayers).

One key or unique issue with these approaches is that sensing takes place via the attachment of molecules of the desired species to the sensor end groups bringing it into an irreversible saturated state via physical adsorption or chemical adsorption. More importantly, in most instances, the nature of the sensor is such that its mean-time-before-failure (MTBF) is limited (e.g., sensors that are cantilever-based or any other rendition that contains moving parts). This poses a reliability concern especially when working with embedded sensors such as BioMEMS sensors, or sensors intended for remote, difficult to access locations such as spacecraft or robotic probes for planetary exploration.

Traditional approaches for developing state-of-the-art sensing technologies targeted for specific applications are costly, mostly due to the expensive laboratory and facilities infrastructure required for their fabrication and high-volume production. In addition, the hybrid integrated approach of the different circuit components makes size reduction difficult. Reduced size is a relevant requirement in applications such as Bio-embedded devices. Traditionally, even those sensing devices developed at the nanostructure level perform only a unifunctional, specific sensing task and not a dual switching/sensing function. Switching enables the device to autonomously respond to changes in normal conditions and trigger appropriate responses, and then revert to baseline operation once the environment being sensed has returned to normal.

For this dual functionality, the current state of the art on nano-switch/sensors are based on metal oxide components (e.g., ZnO) with circuits consisting of mechanical actuators such as cantilevers, which include many non-trivial fabrication steps. Furthermore, the mechanical nature of these conventional sensors limits reliability due to a reduction on the MTBF. This level of complexity may be a critical disadvantage that can hinder the transition of the device from laboratory demonstration to practical working applications.

SUMMARY

The following presents a simplified summary in order to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

The innovation disclosed and claimed herein, in one aspect thereof, comprises a nanostructure device adapted to perform dual functions as a nano-switching/sensing device. The device includes a doped substrate, an insulating layer disposed on the substrate (e.g. silicon substrate), an electrode formed on the insulating layer, and at least one layer of graphene formed on the electrode. At least one layer of graphene provides an electrical connection between the electrode and the substrate and is the electroactive element in the device.

In another aspect of the innovation, the nanostructure device is based on a use of graphene to develop a diode at the nanoscale level.

In yet another aspect of the innovation, based on experimental performance of the nanostructure device, the innovation exhibits dual use functionality (e.g., switching and sensing) and reversibility characteristics.

In still another aspect of the innovation, the nanostructure device can be fabricated using either n-doped or p-doped silicon substrate, which adds another dimension for applications of the device by enhancing its compatibility with other silicon-based nanoelectronic circuits.

In yet another aspect, the innovation has no moving parts, which is contrary to conventional nanosensors that rely on cantilevers and other mechanical/moving parts. As a result, the innovation offers reliable performance with a long mean-time-before-failure (MTBE).

To accomplish the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

In addition, there is no reported work on a graphene-based dual use nano-switch/sensor device for toxic gases. Consequently, the innovation reported in this disclosure represents the first proof of concept of that possibility.

DETAILED DESCRIPTION

Figure 1:
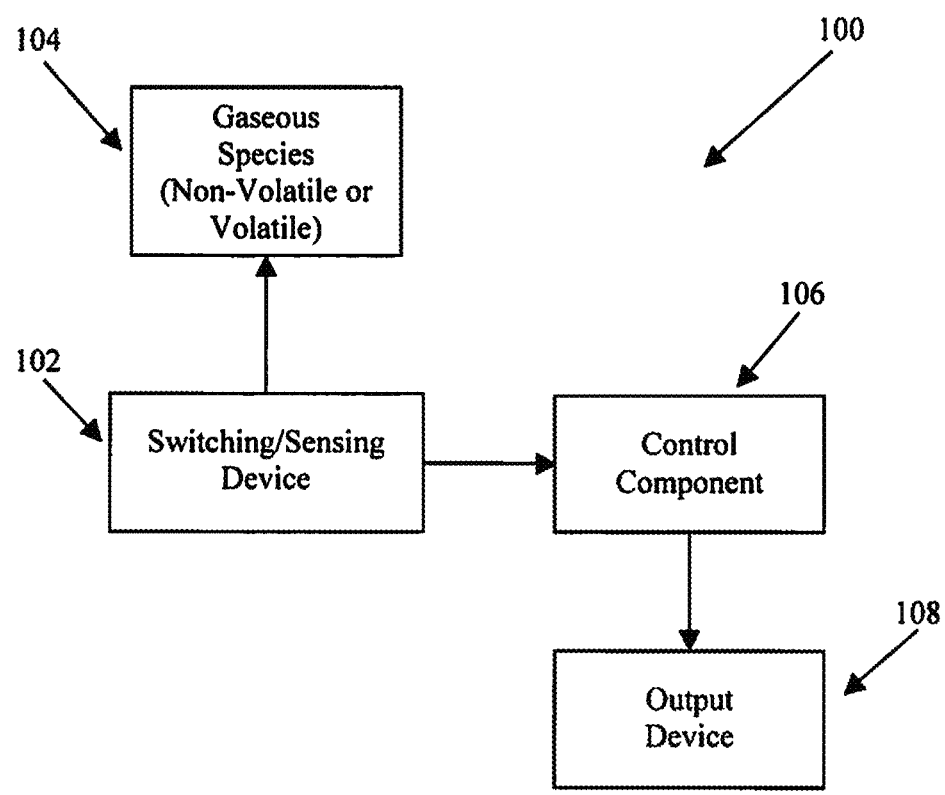
FIG. 1 illustrates an example system incorporating a dual function nanostructure device in accordance with the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While specific characteristics are described herein (e.g., thickness), it is to be understood that the features, functions and benefits of the innovation can employ characteristics that vary from those described herein. These alternatives are to be included within the scope of the innovation and claims appended hereto.

Further, in view of the aspects and features described, methodologies that may be implemented in accordance with embodiments of the subject innovation will be better appreciated with reference to the figures. While for purposes of simplicity of explanation, the methodologies are shown and described as a series of drawings representing steps or acts associated with the methodologies, it is to be understood and appreciated that the claimed subject matter is not limited by the order of the drawings, as some drawings may occur concurrently with other drawings and/or in different orders than what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated drawings may be required to implement the methodologies described hereinafter.

The innovation described herein and shown in the figures, in one aspect thereof, is representative of a nanostructure that may be a dual use nano-switching/sensing device comprised of a graphene-based nano-Schottky diode. The performance of the innovation has been experimentally tested in an ambient atmosphere as well as under other non-volatile and volatile atmospheres. For example, the innovation has been experimentally tested under ammonia gas ($NH_3$), but could operate under other volatile or toxic gases, such as hydrogen, hydrocarbons, nitrogen oxides, carbon monoxide, carbon dioxide, etc. The resulting experimental data disclosed herein, demonstrates a dual switching/sensing nature (and function) of the innovation. Hence, the acronym nanoSSSD (nano-Switch/Sensor Schottky Diode). Further, the resulting experimental data also reveals a reversible characteristic of the innovation, which makes it suitable for nanosensing applications where access to the sensor and its potential replacement opportunities are limited (e.g., biosensors, harsh environment, etc.).

Specifically, due to the following characteristics of graphene, the innovation has extreme sensitivity to different gaseous species with a remarkable attribute of having reversibility properties, thereby serving as a building block for a volatile species sensor. As is known, graphene is formed from a single layer (one atom thick) of carbon and has a hexagonal shape. Thus, graphene is a 2-dimensional material and, as such, its entire volume is exposed to its surroundings, thereby making it sensitive to the adsorption and desorption of a single gas molecule. Further, graphene's single layer structure makes graphene a zero-gap semiconductor, where the valence band and the conduction band overlap, thereby giving graphene superior electrical conduction and low electrical noise properties. This high electrical conductance also contributes to graphene's sensitivity to the adsorption and desorption of a single gas molecule. Because graphene is sensitive to the adsorption and desorption of gas molecules, the resistivity of graphene also changes, thereby giving the graphene-based innovation its sensing ability. Therefore, the innovation, when operating as a sensor, is able to cycle between active and passive sensing states in response to the presence or absence, respectively, of the gaseous species. Furthermore, graphite is a three-dimensional material that is derived from stacking multiple layers of graphene. The electrical properties of thin layers of graphite will more closely resembled the electrical properties of graphene than those of thick graphite layers. The advantages of using graphite for the present invention include ease of fabrication and compatibility with standard semiconductor device processing techniques. Hence, the current device uses graphite as the sensing element as well as graphene.

In addition, because of the aforementioned sensitivity and diode properties, the device can be used as a switch whose operational stages (i.e., open/close or on/off) could be controlled by a given gaseous species. Consequently, the innovation has great potential as a building block for implementation of a switch/sensor device for harsh, embedded or enclosed environments (e.g., human body, space-based habitats, aircraft, rail, etc.) where the longevity and reusability of the circuit are critical for reliable operation. Furthermore, graphene's excellent electrical and physical properties such as the ability to maintain current densities approximately a million times higher than that of copper, record strength of 200 times greater than steel, and elastic stretching capabilities of up to 20%, will make this device more robust than those made from nano-cantilevers comprised of more fragile metal oxides.

With reference now to the figures, FIG. 1 illustrates an example system 100 implementing the innovation. The system 100 may be a system where the exposure of a volatile or toxic gas may be harmful to humans and/or critical equipment. Some example systems may include airports and mass transportation systems, airplanes, and space platforms that require emissions monitoring, leak detection, engine monitoring, security, fire detection, personal health monitoring, environmental monitoring, etc. The system 100 includes a dual function nano-switching/sensing device 102, a gaseous species 104 introduced to the nano-switching/sensing device 102, a control component 106, and an output device 108.

The nano-switching/sensing device 102 is a graphene-based nano-Switch/Sensor Schottky Diode (nanoSSSD) and will be described in more detail further below in reference to FIGS. 2, 3(A), and 3(B). The control component 106 receives information from the nano-switching/sensing device 102 and outputs a signal to the output device 108. For example, if the nano-switching/sensing device 102 senses a gaseous species 104, the switching portion of the nano-switching/sensing device 102 can automatically actuate thereby sending a signal to the control component 106. The control component 106 in turn can activate the output device 108, which may be in the form of a warning device.

Figure 2:
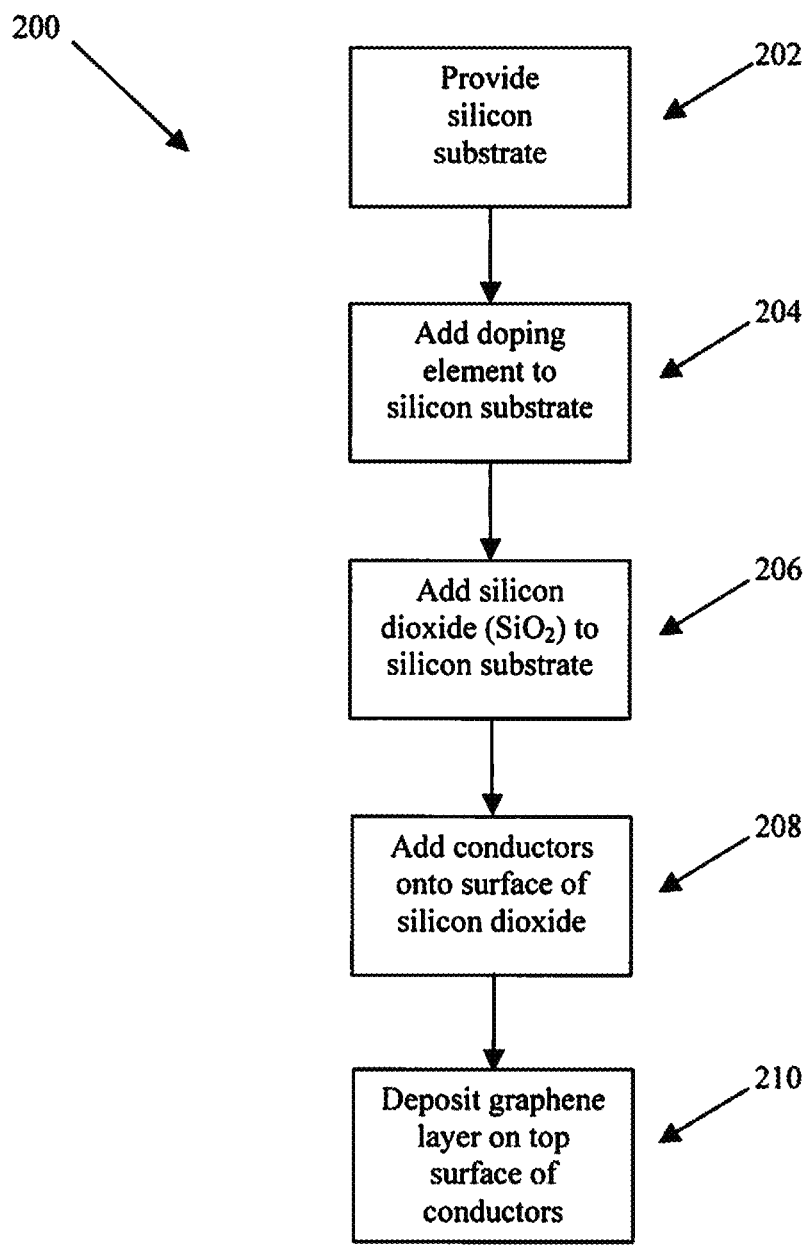
FIG. 2 illustrates an example fabrication process of the dual function nanostructure device in accordance with the innovation.
Figure 3A:
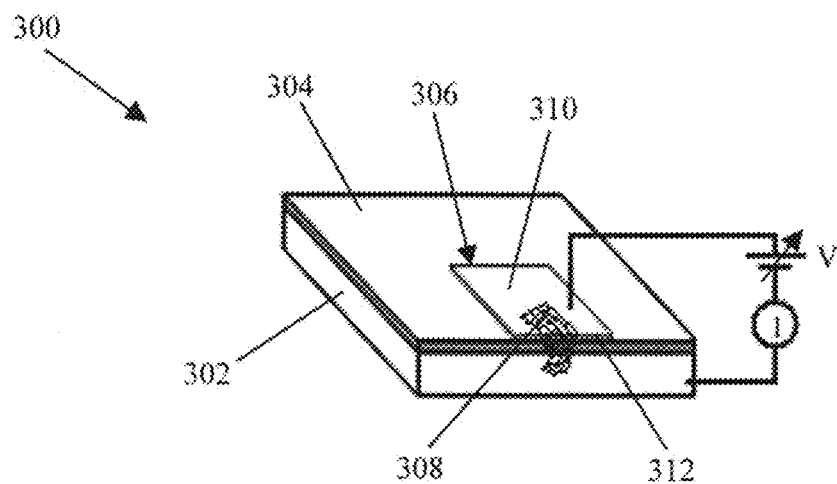
FIG. 3A illustrates an example schematic of dual function nanostructure device in accordance with the innovation.
Figure 3B:
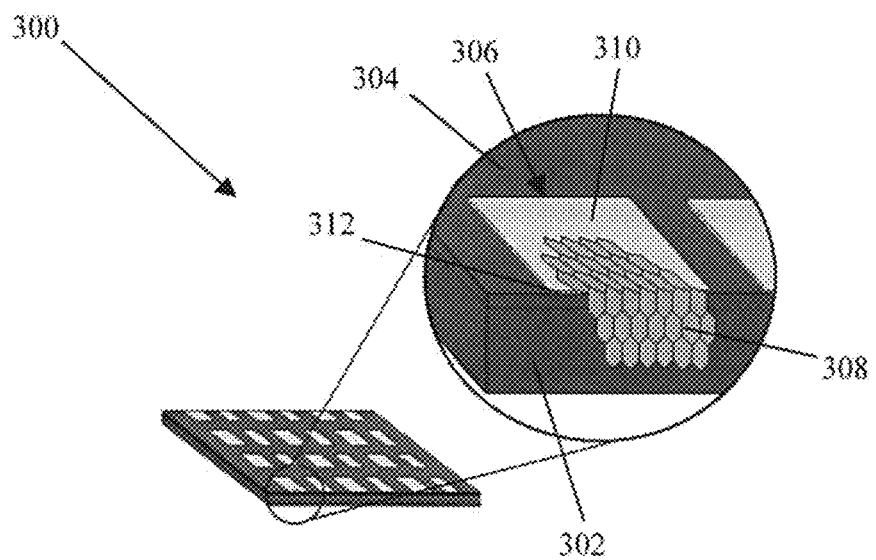
FIG. 3B illustrates an example schematic of a pre-patterned doped substrate in accordance with aspects of the innovation.

With reference to FIGS. 2, 3A, and 3B simultaneously, FIG. 2 illustrates a process 200 to fabricate a nanostructure device 300, shown schematically in FIG. 3A, incorporating the nano-switching/sensing device 102. At step 202, a wafer is provided in the form of a single crystal, such as silicon (Si), to form a substrate 302. At step 204, a doping agent or dopant is added to the substrate 302. The doping agent may be either an n-type (donor) or a p-type (acceptor) dopant. It should be noted that the responsiveness of the nanostructure device 300 differs depending on the substrate doping type. At step 206, an insulator 304 is formed on the substrate 302. In an example embodiment, the substrate is an n-type or a p-type doped silicon (Si) substrate and the insulator 304 is a thermally grown layer of silicon dioxide ($SiO_2$). In the example embodiment, the silicon resistivity of the doped silicon substrate 302 is on the order of 1-10 ohms per centimeter. Further, the thickness of the $SiO_2$ insulating layer 304 has a thickness of approximately 100-300 nm. However, the nanoSSSD is only modestly impacted by oxide thickness and can operate over a wider range of oxide thickness than listed above. Fabrication of the nanostructure device 300 utilizing a silicon-based substrate enhances its compatibility with other silicon-based nanostructures.

At step 208, a pattern of electrodes 306 are formed on the substrate 302 using microfabrication techniques (e.g., sputter deposition, etc.). In an example embodiment shown in FIGS. 4-5, the electrodes 306 are gold (Au) electrodes and are disposed on the substrate 302 in a square checker-board type pattern. In other example embodiments, however, the electrodes 306 may be formed on the substrate 302 in any type of pattern (e.g., circular, rectangular, etc.).

Graphene 308 is deposited on a top surface 310 of each electrode 306 and extends over an edge 312 of the electrode 306 so as to contact the substrate 302, illustrated in FIGS. 3A and 3B. The graphene 308 provides a conductive path between the electrode 306 and the substrate 302, thus forming the nanostructure device 300 and more specifically, a Schottky diode. The graphene 308 may include a single layer of graphene or multiple layers of graphene. Further, the graphene 308 may be produced by microfabrication techniques (e.g., exfoliation methods, chemical vapor deposition, etc.).

In another example embodiment, the graphene 308 is formed on the top surface 310 of at least two electrodes 306 and a semiconducting region, which includes a portion of the substrate 302 and the insulator 304, between the at least two electrodes 306. As mentioned above, graphene 308 is sensitive to the adsorption and desorption of a single gas molecule. In an example embodiment, the semiconducting region, which includes the substrate 302 and/or the insulator 304, may be etched such that the gaseous species to be sensed has direct physical access to both a top and bottom surface of the graphene 308.

Figure 4:
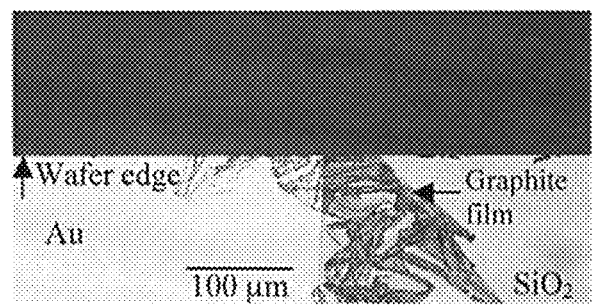
FIG. 4 illustrates an example microscopic image of a graphene film crossing a wafer edge in accordance with the innovation.
Figure 5:
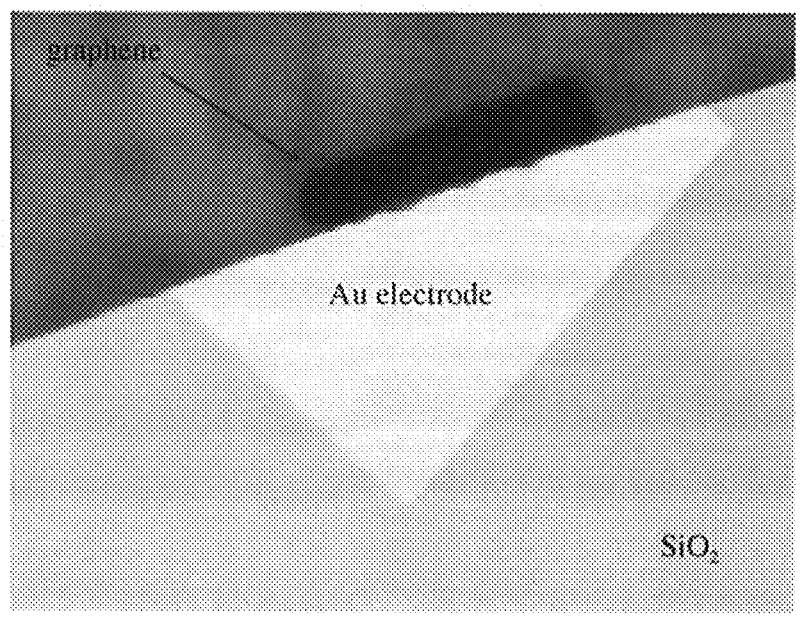
FIG. 5 illustrates an example micrograph illustrating contact of graphene with an electrode in accordance with aspects of the innovation.

FIGS. 4 and 5 represent micro-images of the nanostructure 300. Specifically, FIG. 4 is a top optical view microscopic image magnified 200 times of an actual graphene layer crossing the edge of the substrate 302. FIG. 5 is a micrograph that illustrates the contact of the graphene layer 308 with the electrode 306, which is disposed on the $SiO_2$ insulating layer 304.

Referring again to FIG. 3A, a dc voltage may be applied between the electrode 306 and the substrate 302 to thereby activate of the nanostructure device 300. The resulting I-V (Current-Voltage) characteristics of the nanostructure device 300 are illustrated in FIGS. 7-10. As illustrated, when the nanostructure device 300 is exposed to a volatile species (e.g., ammonia ($NH_3$)), the response (diode response) is unambiguously different to that manifested under normal ambient conditions.

Figure 6:
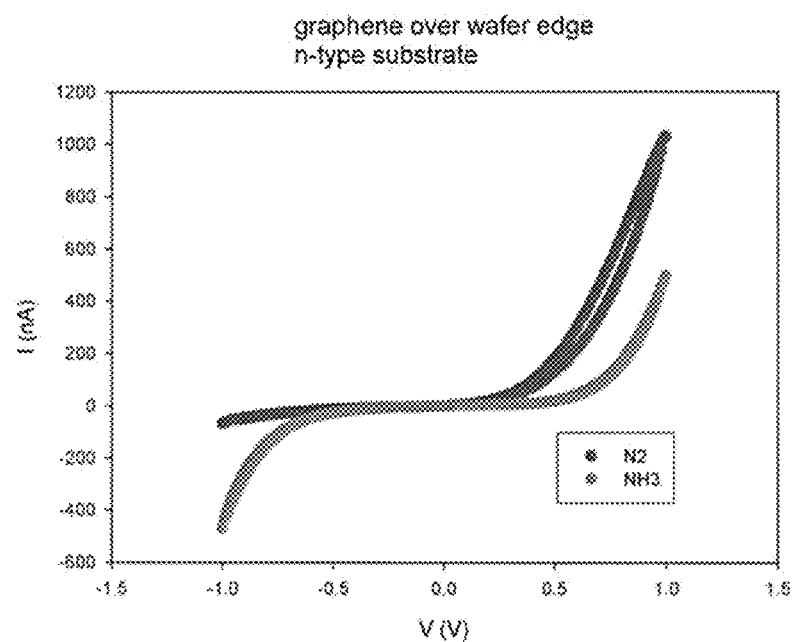
FIG. 6 illustrates an example experimental response of the dual function nanostructure device in accordance with the innovation.
Figure 7:
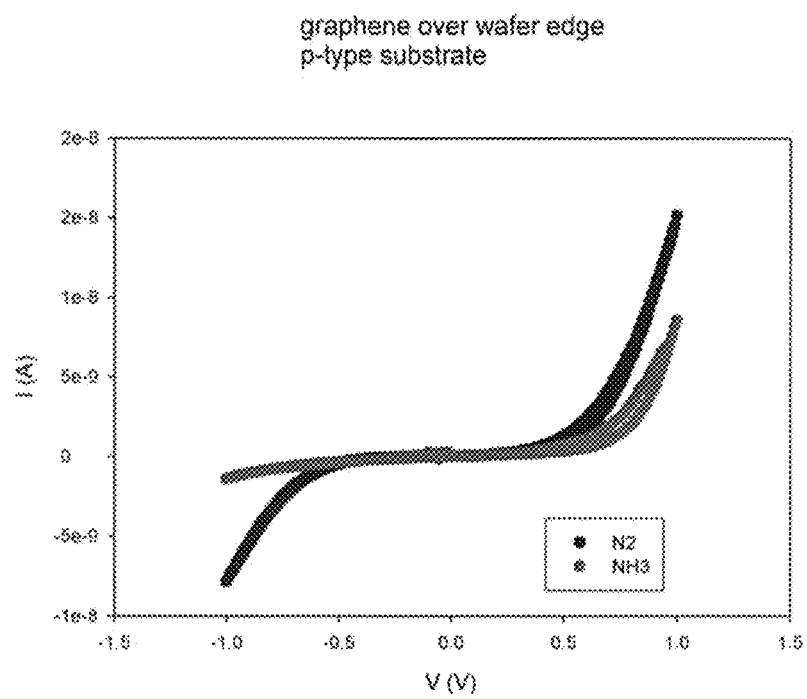
FIG. 7 illustrates an example experimental response of the dual function nanostructure device in accordance with the innovation.

Specifically, FIG. 6 shows the experimental I-V characteristic response of the nanostructrure device 300 for the n-type doped silicon substrate 302 when the atmosphere is changed from a non-volatile species (e.g., nitrogen ($N_2$)) to a volatile species ($NH_3$). Similarly, FIG. 8 illustrates the experimental I-V characteristic response of the nanostructure 300 for the p-type doped silicon substrate 302 when the atmosphere is changed from the non-volatile species ($N_2$) to the volatile species ($NH_3$).

As described above, FIGS. 6 and 7 illustrate how the nanostructure device 300 responds when the nanostructure device 300 is exposed to a volatile species. Also significant, however, is the behavior of the nanostructure device 300 (shown in FIGS. 8 and 9) when the volatile species is removed. Specifically, as illustrated in FIGS. 8 and 9, the performance of the nanostructure device 300 returns to its normal mode of operation as the volatile species is removed.

Figure 8:
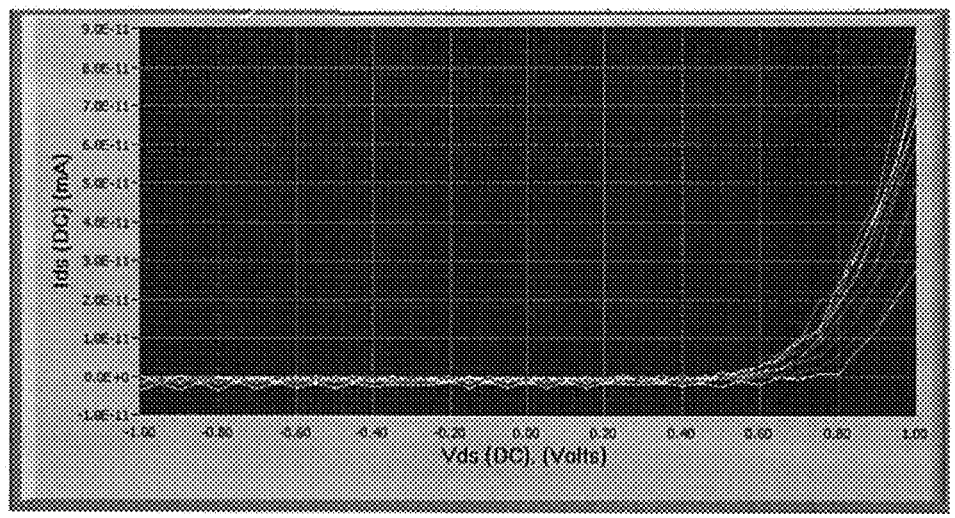
FIG. 8 illustrates an example I-V (Current-Voltage) characteristic of the dual function nanostructure device with the introduction of the volatile species in accordance with the innovation.

Referring to FIG. 8, illustrated are I-V characteristics of the nanostructure device 300 when the volatile gaseous species $NH_3$ is introduced into an ambient atmosphere. As the volatile species $NH_3$ is introduced, the I-V curve shifts to the left. Specifically, prior the introduction of the $NH_3$, the I-V curve is represented by the purple line. As the $NH_3$ is introduced the I-V curve gradually shifts to the left and is represented by the yellow line.

Figure 9:
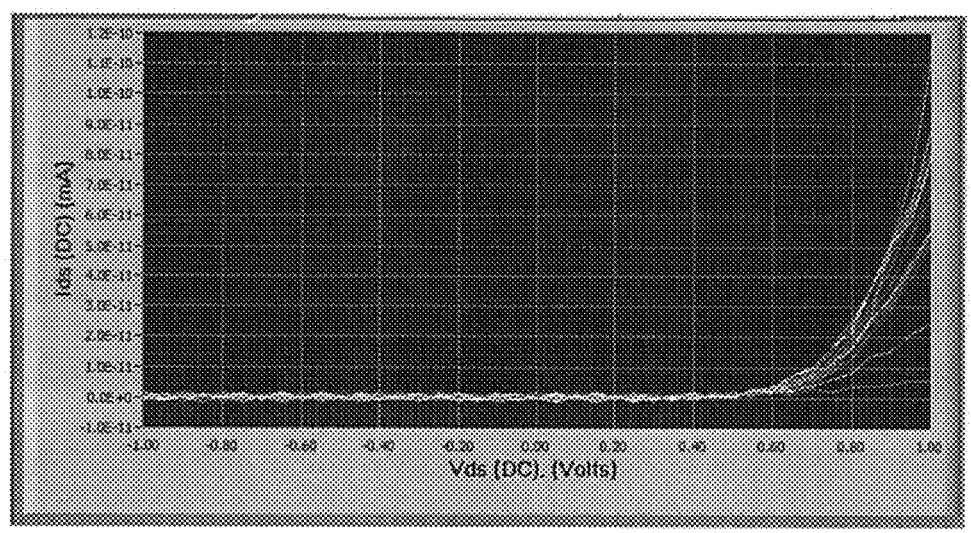
FIG. 9 illustrates an example I-V characteristic of the dual function nanostructure device with the removal of the volatile species in accordance with the innovation.

Conversely, referring to FIG. 9, illustrated are I-V characteristics of the nanostructure device 300 with the removal of the volatile gaseous species $NH_3$ and the atmosphere returns to the ambient atmosphere. As the volatile species $NH_3$ is removed, the I-V curve shifts to the right. Specifically, prior to the removal of the $NH_3$, the I-V curve is represented by the dark blue line. As the $NH_3$ is introduced the I-V curve gradually shifts to the right and is represented by the light blue line.

As clearly illustrated by FIGS. 8 and 9 and as indicated above, the performance of the nanostructure device 300 returns to its normal mode of operation as the volatile species is removed. This reversible feature forms the basis for the functional operation of the nanostructure device 300, thus, resulting in a reliable, long mean-time-before-failure (MTBF) nano-switch/sensor that is ideal for applications where frequent replacement of the nanostructure device 300 is not a viable option. In addition, based on the same feature, the nanostructure device 300 could act as a switch whose performance could be tailored by dispensing or retrieving the particulates of the volatile species.

While, as discussed above, there are other alternate approaches for attaining nanosensors, the innovation discussed here is unique not only because of the use of graphene, but also because of the fully reversible (i.e., reusable) dual nature of the nanostructure device 300 (i.e., nano-switch/sensor). As a result, the innovation presented in this disclosure has many unique and novel features. First, the nanostructure device 300 is based on a use of graphene to develop such a diode at the nanoscale. Second, because of the properties of graphene (i.e., maximization of sensing surface due to 2-dimensional nature, robustness, good electrical conductivity, etc.) the nanostructure device 300 is extremely reliable, e.g., even under a harsh environment (i.e., human body internal environment; extreme cold/hot temperature environments; etc.). Third, contrary to conventional nanosensors, which rely on cantilevers and other mechanical/moving parts, the innovation has no moving parts and, as such, promises to offer reliable performance with a long MTBF. Fourth, based on the performance of the device, the innovation exhibits dual use functionality. Specifically, the device can function as a sensor and a switch. Fifth, the device can be fabricated using either n-doped or p-doped silicon, which adds another dimension for applications of the device by enhancing its compatibility with other silicon-based nanoelectronic circuits. Sixth, the innovation is based on a vertical configuration, which saves highly coveted circuit area, but may also be based on other configurations. Seventh, the fabrication procedure is economical and therefore offers the possibility of low cost implementation when compared to traditional approaches.

The aforementioned functionalities can be either exploited separately or in tandem depending on the specific application, which adds to the versatility of the device. Specifically, the innovation described herein has many potential commercial applications beyond those of traditional devices. For example, research groups have attempted to demonstrate a graphene-based switch with potential for applications in the non-volatile memory market. The device, however, functions only as a switch. In other words, unlike the innovation described herein, the conventional device does not exhibit sensing functions. Further, others have demonstrated, what they claim to be, the world's fastest graphene transistor operational at 26 GHz. This non-silicon based device, however, is not capable of both sensing and switching applications.

The innovation described herein, on the other hand, has the potential to expand the applications of combined switching/sensing graphene based nanoelectronics not only in areas ranging from embedded biomedical devices but also to extremely sensitive detection/switching devices required for earth or space-bound applications on harsh environment (e.g., airplanes turbines; surveillance of airports and mass transportation systems such as subways and trains; space platforms such as the International Space Station (ISS), Crew Exploration Vehicles (CEV), lunar and planetary habitats, etc.).

Specific potential applications of the innovation include the detection of toxic gases such as ammonia, hydrogen, hydrocarbons, nitrogen oxides ($NO_x$) (i.e., NO and $NO_2$), carbon monoxide (CO), and carbon dioxide $CO_2$.

In addition, this device can be used to detect explosives, e.g., in an effort to prevent terrorist attacks. For example, the device can detect 2,4-dinitrotoluene, which is a volatile material found in TNT explosives.

In yet other aspects, the innovation can be connected to a visual and sound alarm that will be autonomously triggered in the presence of gas and return to its passive mode in absent of it. Further, the device can respond differently to each gas and, therefore, may be possible to generate colored signals, for example, where colors correspond to a specific detected gas.

In yet another embodiment, the use of a conducting polymer nanofiber as the active element in the nanoSSSD device is further described in addition to the above. This conducting polymer nanofiber will replace at least one graphene layer mentioned in the above specifications without degradation of device performance.

The innovation described retains all of the aspects of the previous innovation with the additional possibility that this device can also be used to detect UV radiation. Conducting polymers are sensitive to UV radiation via the creation of electron-hole pairs that subsequently interact with adsorbed atoms or molecules on the polymer. In the case of a nanofiber that has an extremely high surface area to volume ratio such interaction can occur at extremely low concentrations which implies a very low detection threshold for UV radiation.

Figure 10:
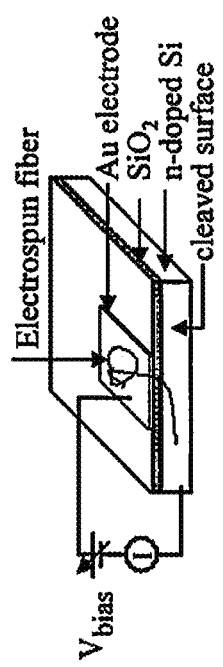
FIG. 10 illustrates the schematic of the device showing the substrate, the polymer nanofiber, and the external electrical connections for device operation.
Figure 11:
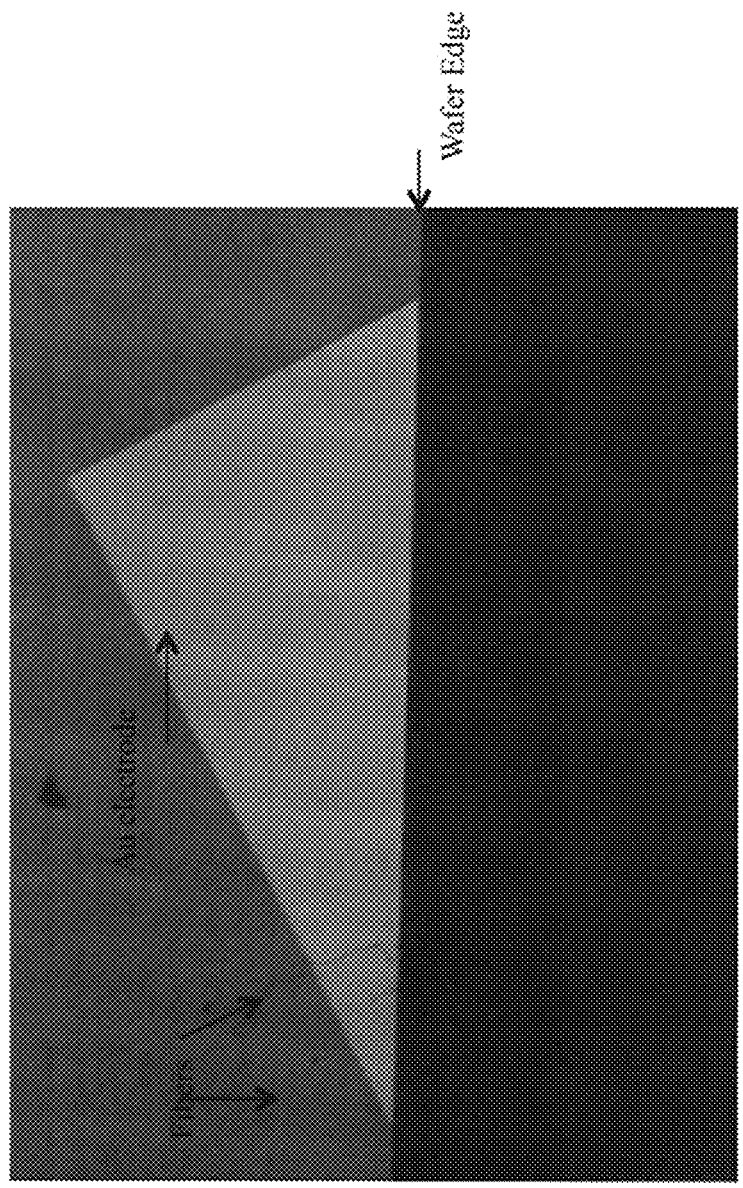
FIG. 11 illustrates an optical microscope image (top view) of the actual substrate, the metal electrode at the substrate edge and the polymer nanofiber crossing the substrate edge.
Figure 12:
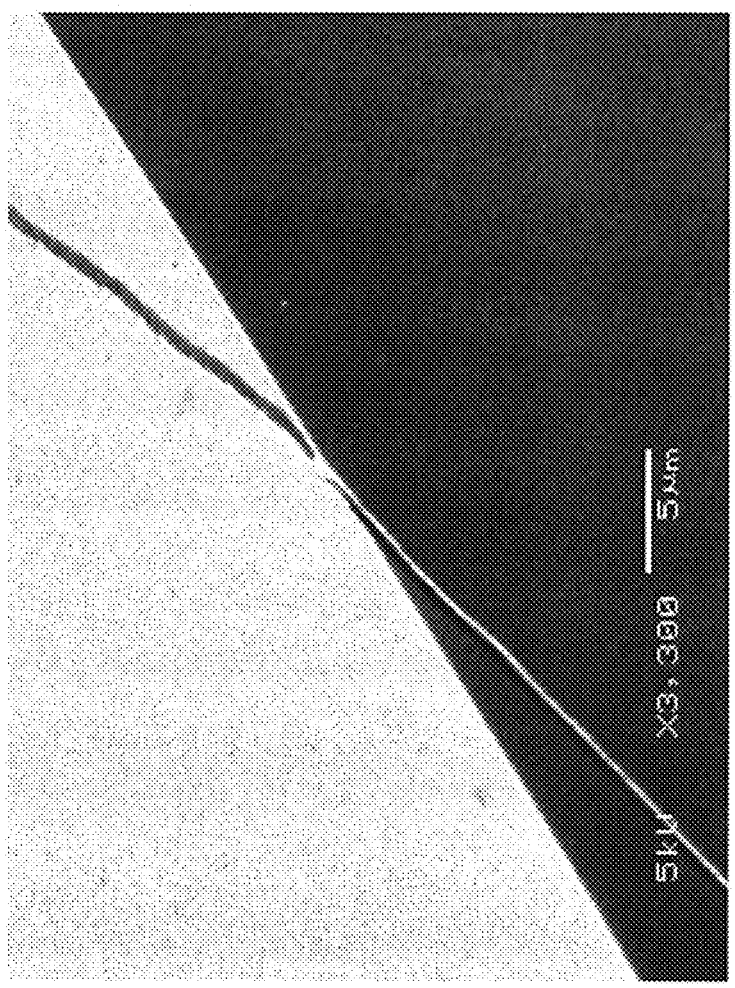
FIG. 12 illustrates a magnified SEM image of a polymer nanofiber crossing the substrate edge.

FIGS. 10, 11 and 12 show the device construction, and the external electrical connections.

Figure 13:
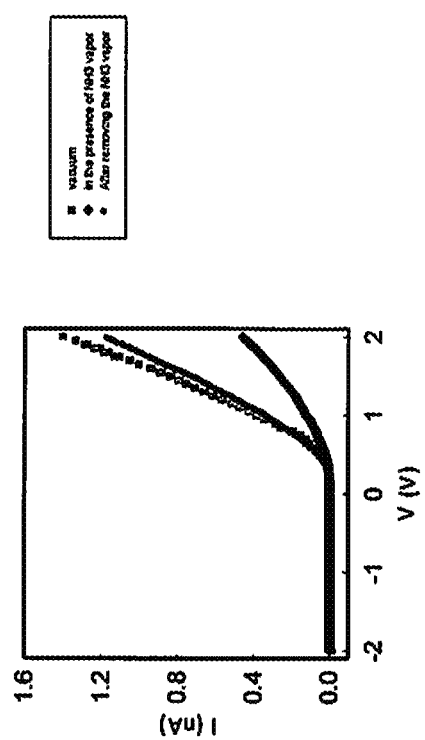
FIG. 13 illustrates the device current-voltage curves under operation. The green curve represents the operation in vacuum; the black curve represents the device operating in a toxic $NH_3$ environment; the blue curve represents the device operating in a toxic free environment after removal of $NH_3$. This shows that the device continues to operate without damage by toxic gases.

FIG. 13 shows the device current-voltage curves in the presence and absence of ammonia vapor. The operation is not affected and the device returns to original operating specifications.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A detection method comprising:
    providing a polymer nanofiber-based nano-switching/sensing device, wherein the polymer nanofiber-based sensing device includes at least one polymer nanofiber electrically connecting a substrate with an electrode disposed on the substrate;
    exposing the polymer nanofiber-based nano-switching/sensing device to a detectable agent such that the detectable agent interacts with the at least one polymer nanofiber; and detecting a first electrical response of the nanofiber-based nano-switching/sensing device resulting from the interaction of the detectable agent with the at least one polymer nanofiber.

2. The detection method of claim 1, wherein the detectable agent comprises ultraviolet radiation.

3. The detection method of claim 1, wherein the detectable agent comprises a first molecule of first volatile gaseous species.

4. The detection method of claim 1, wherein the detectable agent further comprises a second molecule of a second volatile gaseous species different from the first volatile gaseous species.

5. The detection method of claim 4, wherein the first volatile gaseous species comprises one of ammonia, hydrogen, a hydrocarbon, a nitrogen oxide, and carbon dioxide.

6. The detection method of claim 5, wherein the second volatile gaseous species comprises one of ammonia, hydrogen, a hydrocarbon, a nitrogen oxide, and carbon dioxide.

7. The detection method of claim 6, wherein detecting the first electrical response includes generating a warning signal via an alert device.

8. The detection method of claim 7, wherein the warning signal comprises a sound alarm.

9. The detection method of claim 7, wherein the first electrical response varies depending on whether the first molecule or the second molecule in the detectable agent interacts with the at least one polymer nanofiber, wherein the alert device comprises a variable light source configured to generate a first warning light of a first color when the at least one polymer nanofiber interacts with the first molecule and generate a second warning light of a second color when the at least one polymer nanofiber interacts with the second molecule.

10. The detection method of claim 1, wherein the detectable agent comprises 2,4-dinitrotoluene.

11. The detection method of claim 1 further comprising:
removing the polymer nanofiber-based nano-switching/sensing device from exposure to the detectable agent to induce a second electrical response in the polymer nanofiber-based nano-switching/sensing device; and
detecting the second electrical response.

12. The method of claim 11, wherein the polymer nanofiber-based nano-switching/sensing device includes a Schottky diode formed in part by the at least one polymer nanofiber.

13. The method of claim 12, wherein the first electrical response comprises an alteration of the I-V characteristic response of the polymer nanofiber-based nano-switching/sensing device.

14. The method of claim 13, wherein the second electrical response comprises a reversal of the alteration of the I-V characteristic response of the polymer nanofiber-based nano-switching/sensing device such that the I-V characteristic response of the polymer nanofiber-based nano-switching/sensing device returns to what the I-V characteristic response was prior to the interaction of the at least one polymer nanofiber with the detectable agent.

15. The method of claim 14, wherein the detectable agent comprises ultraviolet radiation.

16. The detection method of claim 14, wherein the detectable agent comprises a volatile gaseous species comprising one of ammonia, hydrogen, a hydrocarbon, a nitrogen oxide, and carbon dioxide.

17. The method of claim 11, wherein the substrate comprises a doped substrate.

18. The method of claim 17, wherein the doped substrate is a silicon substrate doped with an n-type doping agent and has a silicon resistivity in the range of 1-10 ohms-centimeter.

19. The method of claim 17, wherein the doped substrate is a silicon substrate doped with an p-type doping agent and has a silicon resistivity in the range of 1-10 ohms-centimeter.

20. The method of claim 17, wherein the polymer nanofiber-based nano-switching/sensing device further comprises an insulating layer comprised of silicon dioxide having a thickness of approximately 100-300 nm disposed between the electrode and the doped substrate.

* * * * *